(12) United States Patent
Turkyilmaz et al.

(10) Patent No.: US 9,795,592 B2
(45) Date of Patent: Oct. 24, 2017

(54) PHARMACEUTICAL FORMULATIONS OF VILDAGLIPTIN

(71) Applicant: Sanovel Ilac Sanayi Ve Ticaret Anonim Sirketi, Istanbul (TR)

(72) Inventors: Ali Turkyilmaz, Istanbul (TR); Ali Hasan Turp, Istanbul (TR); Mehtap Saydam, Istanbul (TR); Onur Ulgen, Istanbul (TR)

(73) Assignee: Sanovel Ilac Sanayi Ve Ticaret Anonim Sirketi, Istanbul (TR)

( * ) Notice: Subject to any disclaimer, the term of this patent is extended or adjusted under 35 U.S.C. 154(b) by 0 days.

(21) Appl. No.: 15/123,818

(22) PCT Filed: Mar. 5, 2015

(86) PCT No.: PCT/EP2015/054631
§ 371 (c)(1),
(2) Date: Sep. 6, 2016

(87) PCT Pub. No.: WO2015/132341
PCT Pub. Date: Sep. 11, 2015

(65) Prior Publication Data
US 2017/0014379 A1   Jan. 19, 2017

(30) Foreign Application Priority Data
Mar. 6, 2014   (TR) .............. a 2014 02685

(51) Int. Cl.
*A61K 31/40*   (2006.01)
*A61K 9/28*   (2006.01)
*A61K 9/20*   (2006.01)

(52) U.S. Cl.
CPC ............ *A61K 31/40* (2013.01); *A61K 9/2009* (2013.01); *A61K 9/2013* (2013.01); *A61K 9/2027* (2013.01); *A61K 9/2054* (2013.01); *A61K 9/28* (2013.01)

(58) Field of Classification Search
None
See application file for complete search history.

(56) References Cited

U.S. PATENT DOCUMENTS

| | | | |
|---|---|---|---|
| 2012/0201885 A1* | 8/2012 | Birringer | A61K 45/06 424/465 |
| 2012/0294939 A1* | 11/2012 | Kowalski | A61K 9/2013 424/465 |

FOREIGN PATENT DOCUMENTS

| | | | | |
|---|---|---|---|---|
| EP | 1841413 | | 10/2007 | |
| EP | 2165703 A3 | | 3/2010 | |
| EP | 2578208 A1 | | 4/2013 | |
| SI | WO 2011012322 A9 * | | 8/2011 | .......... C07D 207/16 |
| TR | EP 2578208 B1 * | | 5/2014 | ............. A61K 31/40 |
| WO | WO 2006/078593 A2 | | 7/2006 | |
| WO | WO 2013/062902 A2 | | 5/2013 | |

OTHER PUBLICATIONS

International Preliminary Report on Patentability (IPRP) and International Search Report (ISR) for International Appl. No. PCT/EP2015/054631, int'l Filing Date Mar. 5, 2015, issued on Sep. 6, 2016.

* cited by examiner

*Primary Examiner* — Ernst V Arnold
*Assistant Examiner* — Kyung Sook Chang
(74) *Attorney, Agent, or Firm* — Seyfarth Shaw LLP

(57) ABSTRACT

The present invention relates to a pharmaceutical formulation comprising therapeutically effective amount of vildagliptin or pharmaceutically acceptable salt thereof and a diluent. Particularly, the ratio of vildagliptin to diluent is in the range of 0.04 to 0.24 (w/w).

16 Claims, No Drawings

PHARMACEUTICAL FORMULATIONS OF VILDAGLIPTIN

CROSS REFERENCE TO RELATED APPLICATIONS

This application is a U.S. national phase application of international application, PCT/EP2015/054631, filed Mar. 5, 2015 which claims the priority of Turkish application No. TR2014/02685, filed Mar. 6, 2014, the disclosure of which is incorporated by reference herein.

FIELD OF INVENTION

The present invention relates to a pharmaceutical formulation comprising therapeutically effective amount of vildagliptin or pharmaceutically acceptable salt thereof and a diluent. Particularly, the ratio of vildagliptin to diluent is in the range of 0.04 to 0.24 (w/w).

BACKGROUND OF INVENTION

Vildagliptin is used for type 2 or non-insulin dependent diabetes. It increases the amount of insulin produced by the body. It also decreases the amount of glucagon which is produced by the body. Because of these effects, vildagliptin can help to control blood sugar levels in people with diabetes. Vildagliptin is used in combination with other medicines which help to control blood sugar levels.

DPP-IV inhibitors work by blocking the action of DPP-IV, an enzyme which destroys the hormone incretin. There are two types of incretin hormones found in the body, called glucagon-like peptide-1 (GLP-1) and glucose-dependent insulinotropic peptide (GIP). These hormones are naturally produced by the body in response to food intake. Their function is to help the body produce more insulin only when it is needed and reduce the amount of glucose being produced by the liver when it is not needed. Vildagliptin works by binding to DPP-IV and preventing it from breaking down the GLP-1 and GIP. This increases the levels of these hormones in the body and so increases their effect on controlling blood sugar.

Formula I

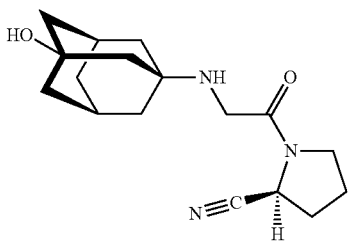

Its chemical name is (S)-{[(3-hydroxyadamantan-1-yl)amino]acetyl}pyrrolidine-2-carbonitril and its chemical structure is shown in the Formula I.

Vildagliptin is marketed under the trademark Galvus® in 50 mg dosage forms by NOVARTIS. It is used against diabetes mellitus, but particularly in treating type 2 diabetes. Galvus® includes lactose anhydrose, microcrystalline cellulose, sodium starch glycolate and magnesium stearate.

In currently commercially available dose of vildagliptin formulation, microcrystalline cellulose is used as a diluent. In contrast, in this present invention, dibasic calcium phosphate was used as a diluent to achieve improved compression and flowability in the formulation.

There are various patents and applications available in the patent literature in relation to vildagliptin formulations. In the patent application EP1841413A2 and EP2165703A3, direct compression is used to develop tablet formulation of DPP-IV inhibitor compounds, especially vildagliptin or an acid addition salt thereof.

It is known that DPP-IV inhibitors with primary or secondary amino group show incompatibilities, degradation problems or extraction problems with some excipients especially excipients that have acidic properties. Vildagliptin has also a secondary amino group on its chemical structure. In solid dosage forms, it may react with many excipients or impurities of excipients, although vildagliptin itself is very stable.

In this invention, diluent is used in a specific ratio in order to achieve desired release profile with desired tablet weight and desired flow during the process. Dibasic calcium phosphate has been chosen as a diluent to achieve high stability in the solid dosage form of vildagliptin.

DESCRIPTION OF THE INVENTION

The present invention relates to a pharmaceutical formulation comprising;
 a) vildagliptin or pharmaceutically acceptable salt thereof, and
 b) a diluent,
wherein the ratio of vildagliptin to diluent is in the range of in the range of 0.04 to 0.24 (w/w).

In one embodiment, in the formulation of this present invention, the ratio of vildagliptin to diluent is in the range of in the range of 0.04 to 0.24 (w/w), preferably 0.04 to 0.23 (w/w) and more preferably it is 0.1 to 0.21 (w/w).

In prior art, the patent application EP1841413A2 and EP2165703A3 disclose a direct compression of vildagliptin tablet formulation in a limited ratio of vildagliptin to diluent. It is often difficult to achieve desired dissolution profile in all the strengths. To overcome such problem it is always necessary to optimize size and surface area of a tablet. In comparison to prior art, in this present invention, it has been found that with a lower ratio of vildagliptin to diluent has given desired dissolution profile. With this ratio, more uniform dissolution profile has also been achieved due to an increase in weight and surface area of the tablet.

In this embodiment diluent is selected from the group comprising dibasic calcium phosphate, inorganic salts, sorbitol, tribasic calcium phosphate, dextrose, trehalose, microcrystalline cellulose, lactose, starch, sodium carbonate, sodium bicarbonate, calcium carbonate, dextrose, sucrose, maltodextrine, isomalt, xylitol, heavy magnesium carbonate or mixtures thereof, preferably it is dibasic calcium phosphate.

The pharmaceutical formulation of this present invention was tested for its dissolution profile measured in 900 mL of 0.1 N HCl at 50 rpm named as USP II (Paddle).

In direct compression for the tablet development process, diluent choice is important to provide adequate flow of powder mixture. It should be both compatible with active agent and other excipients and should not cause any stability problem. In general, DPP-IV inhibitors are not very stable compounds. Especially, in solid dosage forms, amine group containing DPP-IV inhibitors such as vildagliptin may react with many excipients or impurities of excipients. In prior art, microcrystalline cellulose has been used as a diluent for vildagliptin tablet formulation. However, microcrystalline cellulose contains high humidity and it is known that vildagliptin is very sensitive to humidity. In this invention, to ensure flowability of formulation dibasic calcium phosphate has been used and it has been surprisingly found that it provides high stability.

The stability assay has been performed by HPLC with isocratic mobile phase at a wavelength of UV 210 nm at 35±10° C. of column temperature.

In one embodiment, the ratio of vildagliptin to dibasic calcium phosphate is in the range of 0.04 to 0.24 (w/w), preferably 0.04 to 0.23 (w/w) and more preferably it is 0.1 to 0.21 (w/w).

Dibasic calcium phosphate has given good flow and compaction properties to the formulation due to its bulk density. It has been surprisingly found that the specific ratio of vildagliptin to dibasic calcium phosphate surprisingly provides low friability.

In this embodiment, friability test has been performed with a drum with an internal diameter between 283-291 mm and a depth between 36-40 mm by rotating the drum 100 times, with 25±1 r/min rotation speed.

Furthermore, by using this specific ratio of vildagliptin to dibasic calcium phosphate, tablet compaction speed has been increased without any problem such as content uniformity. It has been observed that the compaction speed is between 100.000 tb/h. to 40.000 tb/h.

In addition, in a tablet formulation the ratio of diluent to disintegrant is also crucial to achieve desired dissolution profile and optimum disintegration. In this invention, it has been found that the optimum ratio of dibasic calcium phosphate to croscarmellose sodium is in the range of 2 to 27 (w/w), preferably 5 to 20 (w/w) and more preferably it is 8 to 17 (w/w). It has been surprisingly found that when this ratio increases, excess amount of dibasic calcium phosphate causes an increase on disintegration, a decrease on dissolution properties of tablets and undesired stains on tablets. On the other side, a decrease in ratio of dibasic calcium phosphate to croscarmellose sodium causes destruction in the matrix and hence problems in dissolution. Therefore, in this invention an optimum ratio of dibasic calcium phosphate to croscarmellose sodium has been provided in order to achieve desired matrix and dissolution without any physical problems on tablets.

Suitable disintegrants may include, but not limited to croscarmellose sodium, carboxy methyl cellulose calcium, alginic acid and alginates, ion-exchange resins, magnesium aluminum silica, sodium dodecyl sulphate, sodium carboxy methyl cellulose, polyvinylpyrrolidone, povidone, crospovidone, docusate sodium, guar gam, low-substitute HPC, HPMC, polyacrylin potassium, poloxomer, sodium alginate, sodium glysin carbonate, sodium lauryl sulphate, sodium starch glycolate, soy polysaccharide, gellan gum, xanthan gum, calcium silicate and mixtures thereof.

Suitable binders may include but not limited to polyvinylpyrrolidone, sugars, glycose syrups, natural gums, guar gum, gelatins, pullulan, agar, alginate, sodium algynates, K-Karagen, glycyrrhizin, polymetacrylates, kollagen, agar, algynate, sodium alginate, hyaluronic acid, pectin, tragakanti gum, carboxymethyl cellulose, polyethylene glycol, polyvinyl alcohol, polyvinyl acetate and their copolymers, cellulose derivatives such as hydroxypropyl methyl cellulose, carboxy methyl cellulose, methyl cellulose, microcrystalline cellulose, polyvinylalcohol, carrageenan, carbomer, poloxamer, polyacrylamide, aluminum hydroxide, benthonite, laponite, setosteraryl alcohol, polyoxyethylene-alkyl ethers, acacia mucilage, polydextrose, polyethylene oxide, xylitol, sucrose stearate, and mixtures thereof.

Suitable lubricants may include but not limited to magnesium stearate, sodium stearyl fumarate, polyethylene glycol, sodium lauryl sulphate, magnesium lauryl sulphate, fumaric acid, glyceryl palmitostearate, hydrogenated natural oils, zinc stearate, calcium stearate, silica, talc, stearic acid, polyethylene glycol, paraffin and mixtures thereof.

Suitable glidants may include but not limited to colloidal silicon dioxide, aluminium silicate and mixtures thereof.

Coating may also optionally be used for moisture protection. It can be selected from the group comprising polyvinyl alcohol-polyethylene glycol copolymers (Kollicoat IR), polyvinyl alcohol or copolymers or mixtures thereof (Opadry AMB), Ethylcellulose Dispersions (Surelease), Kerry-HPC, polyethylene glycol, polyvinylprolidone, polyvinylprolidone-vinyl acetate copolymer (PVP-VA) and all kinds of Opadry™, as well as pigments, dyes, titanium dioxide, iron oxide, talc and polymethylmetacrylate copolymers (Eudragit).

In this present invention, to achieve desired dissolution and stability with an improved process, these formulations have been designed, comprising the following:

a. 14.0-16.0% by weight of vildagliptin
b. 70.0-80.0% by weight of dibasic calcium phosphate
c. 3.0-25.0% by weight of croscarmellose sodium
d. 0.1-25.0% by weight of polyvinylpyrrollidone
e. 0.1-3.0% by weight of colloidal silicon dioxide
f. 0.01-5.0% by weight of magnesium stearate
g. Optionally, coating and, a. 14.0-16.0% by weight of vildagliptin
b. 70.0-80.0% by weight of dibasic calcium phosphate
c. 3.0-25.0% by weight of croscarmellose sodium
d. 0.1-25.0% by weight of polyvinylpyrrollidone
e. 0.1-3.0% by weight of colloidal silicon dioxide
f. 0.01-2.0% by weight of sodium stearyl fumarate
g. Optionally, coating Example 1: Compaction

| ingredients | Amount (%) |
| --- | --- |
| vildagliptin | 15.6 |
| dibasic calcium phosphate | 74.5 |
| croscarmellose sodium | 5.0 |
| Polyvinylpyrrollidone (PVP 25) | 3.1 |
| colloidal silicon dioxide | 0.6 |
| magnesium stearate | 1.1 |

The production of the formulation is carried out as follows: Vildagliptin, colloidal silicone dioxide (Aerosil 200) and a part of dibasic calcium phosphate anhydride (Fujicalin SG) are sieved and mixed. Croscarmellose sodium, polyvinylpyrrollidone (PVP 25) and other part of dibasic calcium phosphate are added to the mixture (Ac-Di-Sol) and mixed. The mixture is compacted in compactor and sieved. Magnesium stearate is sieved and added into obtained dry granules and mixed. Final mixture is pressed into tablets. Optionally, tablets are coated for moisture protection.

Example 2: Direct Compression

| ingredients | Amount (%) |
|---|---|
| vildagliptin | 15.6 |
| dibasic calcium phosphate | 74.5 |
| croscarmellose sodium | 5.0 |
| Polyvinylpyrollidone (PVP 25) | 3.1 |
| colloidal silicon dioxide | 0.6 |
| Sodium stearyl fumarate | 1.1 |

The production of the formulation is carried out as follows: Vildagliptin, colloidal silicone dioxide (Aerosil 200) and a part of dibasic calcium phosphate anhydride (Fujicalin SG) are sieved and mixed. Croscarmellose sodium, polyvinylpyrollidone (PVP 25) and other part of dibasic calcium phosphate are added to the mixture (Ac-Di-Sol) and mixed. The mixture is compacted in compactor and sieved. Sodium stearyl fumarate is sieved and added into obtained dried granules and mixed. Final mixture is pressed into tablets. Optionally, tablets are coated for moisture protection.

TABLE 1 friability test

| | diluent | | | | |
|---|---|---|---|---|---|
| vildagliptin | 0.01 | 0.04 | 0.18 | 0.24 | 0.35 |
| friability | 0.3 | 0.1 | 0.1 | 0.1 | 0.5 |

Friability test has been performed by rotating the drum 100 times, with 25±1 r/min rotation speed.

TABLE 2 dissolution profile

| Zaman (min) | Vildagliptin 50 mg Tablet |
|---|---|
| 0 | 0 |
| 5 | 76 |
| 10 | 89 |
| 15 | 95 |
| 20 | 97 |
| 30 | 97 |
| 45 | 98 |
| 60 | 98 |

The pharmaceutical formulation of this present invention was tested for its dissolution profile measured in 900 mL of 0.1 N HCl at 50 rpm named as USP II (Paddle).

The invention claimed is:

1. A pharmaceutical formulation comprising;
a) vildagliptin or pharmaceutically acceptable salt thereof, and
b) a diluent comprising dibasic calcium phosphate,
wherein the ratio of vildagliptin to diluent is in the range of 0.04 to 0.24 (w/w) and wherein when the pharmaceutical formulation is pressed into a tablet, the tablet has a friability of 0.1.

2. The pharmaceutical formulation according to claim 1, wherein the ratio of vildagliptin to diluent is in the range of in the range of 0.1 to 0.21 (w/w).

3. The pharmaceutical formulation according to claim 1, wherein the diluent further comprises one or more substances selected from inorganic salts, sorbitol, tribasic calcium phosphate, dextrose, trehalose, microcrystalline cellulose, lactose, starch, sodium carbonate, sodium bicarbonate, calcium carbonate, sucrose, maltodextrine, isomalt, xylitol, and heavy magnesium carbonate.

4. The pharmaceutical formulation according to 1, wherein the ratio of vildagliptin to dibasic calcium phosphate is in the range of 0.1 to 0.21 (w/w).

5. The pharmaceutical formulation according to claim 1, wherein the formulation further comprises croscarmellose sodium, wherein the ratio of dibasic calcium phosphate to croscarmellose sodium is in the range of 2 to 27 (w/w).

6. The pharmaceutical formulation according to claim 1 comprising
 a. 14.0-16.0% by weight of vildagliptin;
 b. 70.0-80.0% by weight of dibasic calcium phosphate;
 c. 3.0-25.0% by weight of croscarmellose sodium;
 d. 0.1-25.0% by weight of polyvinylpyrollidone;
 e. 0.1-3.0% by weight of colloidal silicon dioxide;
 f. 0.01-5.0% by weight of magnesium stearate; and
 g. optionally, coating.

7. The pharmaceutical formulation according to claim 1 comprising
 a. 14.0-16.0% by weight of vildagliptin;
 b. 70.0-80.0% by weight of dibasic calcium phosphate;
 c. 3.0-25.0% by weight of croscarmellose sodium;
 d. 0.1-25.0% by weight of polyvinylpyrollidone;
 e. 0.1-3.0% by weight of colloidal silicon dioxide;
 f. 0.01-2.0% by weight of sodium stearyl fumarate; and
 g. optionally, coating.

8. The pharmaceutical formulation according to claim 1 comprising;
 a. 15.6% by weight of vildagliptin;
 b. 74.5% by weight of dibasic calcium phosphate;
 c. 5.0% by weight of croscarmellose sodium;
 d. 3.1% by weight of polyvinylpyrollidone;
 e. 0.6% by weight of colloidal silicon dioxide;
 f. 1.1% by weight of magnesium stearate; and
 g. optionally, coating.

9. The pharmaceutical formulation according to claim 1 comprising;
 a. 15.6% by weight of vildagliptin;
 b. 74.5% by weight of dibasic calcium phosphate;
 c. 5.0% by weight of croscarmellose sodium;
 d. 3.1% by weight of polyvinylpyrollidone;
 e. 0.6% by weight of colloidal silicon dioxide;
 f. 1.1% by weight of sodium stearyl fumarate; and
 g. optionally, coating.

10. The pharmaceutical formulation according to claim 5, wherein the ratio of dibasic calcium phosphate to croscarmellose sodium is in the range of 5 to 20 (w/w).

11. The pharmaceutical formulation according to claim 10, wherein the ratio of dibasic calcium phosphate to croscarmellose sodium is in the range of 8 to 17 (w/w).

12. The pharmaceutical formulation according to claim 5, further comprising one or more disintegrants in addition to croscarmellose sodium.

13. The pharmaceutical formulation according to claim 5, further comprising one or more binders.

14. The pharmaceutical formulation according to claim 5, further comprising one or more lubricants.

15. The pharmaceutical formulation according to claim 5, further comprising one or more glidants.

16. The pharmaceutical formulation according to claim 5, further comprising a coating.

* * * * *